US007989596B2

(12) United States Patent
McIntyre

(10) Patent No.: US 7,989,596 B2
(45) Date of Patent: Aug. 2, 2011

(54) METHOD OF ALTERING THE BINDING SPECIFICITY OF MONOCLONAL ANTIBODIES BY OXIDATION-REDUCTION REACTIONS

(75) Inventor: John A. McIntyre, Indianapolis, IN (US)

(73) Assignee: Redox-Reactive Reagents LLC, Beech Grove, IN (US)

( * ) Notice: Subject to any disclaimer, the term of this patent is extended or adjusted under 35 U.S.C. 154(b) by 986 days.

(21) Appl. No.: 11/857,608

(22) Filed: Sep. 19, 2007

(65) Prior Publication Data

US 2009/0071842 A1 Mar. 19, 2009

(51) Int. Cl.
*C07K 16/00* (2006.01)
*A61K 39/395* (2006.01)
*C07D 487/22* (2006.01)

(52) U.S. Cl. ..................... 530/388.1; 204/155; 210/758; 424/141.1; 540/145

(58) Field of Classification Search ........................ None
See application file for complete search history.

(56) References Cited

U.S. PATENT DOCUMENTS

2005/0054051 A1 3/2005 Rosen
2005/0101016 A1 5/2005 McIntyre
2005/0260681 A1 11/2005 McIntyre

OTHER PUBLICATIONS

International Search Report and Written Opinion of the International Searching Authority dated Nov. 13, 2008.
Supplementary European Search Report, Nov. 8, 2010, in EP Application No. 08 795 574.6.
EPO Communication Pursuant to Article 94(3) EPC, Nov. 22, 2010.
Dimitrov, J.D., et al., "Antibodies use heme as a cofactor to extend their pathogen elimination activity and to acquire new effector functions", Journal of Biochemistry, vol. 282, No. 37, Sep. 14, 2007, pp. 26696-26706.
Dimitrov, J.D. et al., "Ferrous ions and reactive oxygen species incrase antigen-binding and anti-inflammatory activities of immunoglobulin G", Journal of Biochemistry, vol. 281, No. 1, Jan. 2006, pp. 439-446.
Wei, Z., et al., "Identification of a single tryptophan residue as critical for binding activity in a humanized monoclonal antibody against respiratory syncytial virus", Analytical Chemistry, vol. 79, No. 7, Apr. 1, 2007, pp. 2797-2805.
Abraham, R., et al., "The influence of periodate oxidation on monoclonal antibody avidity and immunoreactivity", Journal of Immunological Methods, vol. 144, No. 1, Jan. 1, 1991, pp. 77-86.
McIntyre, J.A., et al., "AutoantibodypPotential of cancer therapeutic monoclonal antibodies", International Journal of Cancer, vol. 127, No. 2, Jul. 15, 2010, pp. 491-496.

*Primary Examiner* — David Romeo
(74) *Attorney, Agent, or Firm* — Antonelli, Terry, Stout & Kraus, LLP.

(57) ABSTRACT

The binding specificity of a monoclonal antibody is altered by exposing the monoclonal antibody to an oxidizing agent or an electric potential.

5 Claims, 7 Drawing Sheets

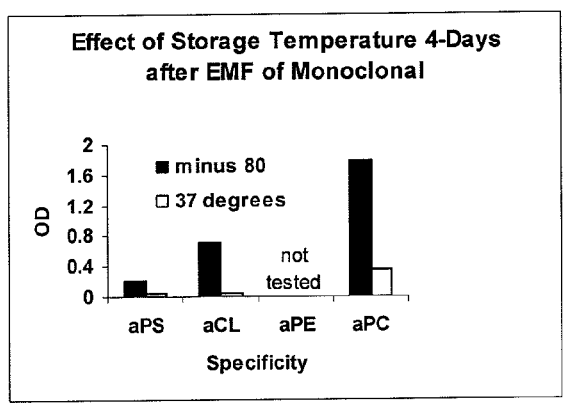 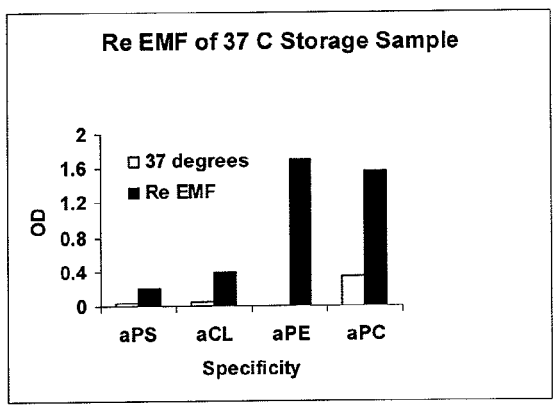
Figure 12A                                    Figure 12B

METHOD OF ALTERING THE BINDING SPECIFICITY OF MONOCLONAL ANTIBODIES BY OXIDATION-REDUCTION REACTIONS

FIELD OF INVENTION

The present invention relates to a method of reversibly altering the binding specificity of monoclonal antibodies.

BACKGROUND OF THE INVENTION

The present inventor has previously reported the discovery that blood and other bodily fluids from normal individuals contain a significant number of autoantibodies, that, when treated with an oxidizing agent, become capable of binding self antigens. See, for example, the following publications:

McIntyre, J A. "The appearance and disappearance of antiphospholipid antibodies subsequent to oxidation-reduction reactions." *Thromb. Res.* 2004; 114:579-87.

McIntyre, J A, Wagenknecht, D R, & Faulk, W P. "Autoantibodies unmasked by redox reactions." *J. Autoimmun* 2005; 24:311-17.

McIntyre, J A, Wagenknecht, D R, & Faulk, W P. "Redox-reactive autoantibodies: Detection and physiological relevance." *Autoimm. Rev.* 2006; 5:76-83.

McIntyre, J A, Chapman, J, Shavit, E, Hamilton, R L, DeKosky, S T. "Redox-reactive autoantibodies in Alzheimer's patients' cerebrospinal fluids: Preliminary studies." *Autoimmunity*, 2007; 40:390-6.

McIntyre, J A, Hamilton, R L, DeKosky, S T. "Redox-reactive autoantibodies in cererebrospinal fluids." *Ann. N.Y. Acad. Sci.* 2007; 1109: 296-302.

U.S. Patent Application Publication No. 2005/0260681 A! and U.S Patent Application Publication No. 2005/0101016 A1.

In these publications, it was reported that blood from normal individuals contains a significant number of autoantibodies, in a wide variety of isotypes and specificities, but that these autoantibodies become detectible only when certain body fluids or blood are exposed to oxidation, by, for example an oxidizing agent or electric current, according to a method described therein. It was reported that samples such as blood, plasma, serum, breast milk, cerebrospinal fluid, and purified immunoglobulin fractions can be treated by oxidation and then assayed with a variety of self antigens and other types of antigens to identify masked autoantibodies that can be unmasked by oxidation. Autoantibodies that have been unmasked by oxidation include the following in Table 2:

TABLE 2

Masked autoantibodies identified to date after redox conversion of normal plasma or IgG.

| Specificity Assay | Method of Detection |
|---|---|
| Glutamic acid decarboxylase (GAD) | RIA |
| Tyrosine phosphatase (IA-2) | RIA |
| Antiphospholipid antibodies: aPS, aPE, aCL, aPC | ELISA |
| Lupus anticoagulant (LA) | APTT, dRVVT |
| Antinuclear antibodies (ANA) | RELISA ® |
| Anti-nucleolus | immunofluorescence |
| Anti-lamin, nuclear membranes | immunofluorescence |
| Anti-mitochondria | immunofluorescence |
| Anti-Golgi | immunofluorescence |
| Anti-granulocyte, neutrophil, monocyte | Flow Cytometry (FACS) |

TABLE 2-continued

Masked autoantibodies identified to date after redox conversion of normal plasma or IgG.

| Specificity Assay | Method of Detection |
|---|---|
| Anti-B lymphocytes | FACS |
| Anti-myeloperoxidase | ELISA |
| Anti-tumor cell lines | Western blot |
| Anti-trophoblast | immunofluorescence |
| Anti-factor VIII | ELISA |
| Platelet factor 4/heparin complex | ELISA |
| Anti-beta2-glycoprotein I | ELISA |
| Red Blood cells | Ortho Gel Cards |
| Ro/SS-A | ELISA |
| Anti-human antigens* | Invitrogen ProtoArray ® |

Table 2 abbreviations used:
aCL, anticardiolipin
aPC, antiphosphatidylcholine
aPE, antiphosphatidylethanolamine
aPS, antiphosphatidylserine
APPT, activated partial thromboplastin time
dRVVT, dilute Russell's viper venom time
ELISA, enzyme-linked immunosorbant assay
RIA, radioimmunoassay
*5,000-6,000 of 8,000 human antigens tested by microarray are recognized by redox-sensitive autoantibodies.

It has now been discovered that the binding specificity of monoclonal antibodies can be altered by similar treatments with an oxidizing agent or a direct electric current. This finding is significant, since monoclonal antibodies are typically intended to bind only a specific antigen. However, according to the method described herein, the spectrum of activity of a monoclonal antibody can be broadened to include antigens other than the specific antigen that the monoclonal antibody is intended to bind.

SUMMARY OF THE INVENTION

According to an aspect of the present invention, there is provided a method comprising providing a composition containing a monoclonal antibody, the monoclonal antibody having a binding specificity toward a specific antigen, and exposing the composition to an oxidizing agent or an electric potential sufficient to effect an alteration of the binding specificity of the monoclonal antibody.

According to another aspect of the present invention there is provided a composition comprising a monoclonal antibody having a binding specificity that has been altered by exposure of the monoclonal antibody to an oxidizing agent or an electric potential.

BRIEF DESCRIPTION OF THE DRAWINGS

FIG. 1 is a graph showing the aPS, aCL, aPE, and aPC binding profiles (as measured by optical density, OD) of an antiglycophorin A monoclonal antibody in an adult bovine plasma (ABP) containing diluent buffer that was designated as a "control", and in the identical buffer diluent after exposure of the monoclonal antibody to an electric potential that was designated as "redox" according to an embodiment of the present invention. The same ELISA test parameters were also conducted using a bovine serum albumin (BSA) containing diluent buffer that was designated as a "control" and in the identical buffer diluent after exposure of the monoclonal antibody to an electric potential that was designated as "redox" according to an embodiment of the present invention.

FIG. 2 is a graph showing the aPS, aCL, aPE, and aPC binding profiles (as measured by OD) of a monoclonal anti-CXCR4 antibody diluted in a buffer containing ABP (control), and in an identical buffer after exposure of the monoclonal antibody to an electric potential (redox) according to an embodiment of the present invention. Similarly the monoclonal was diluted into a buffer containing BSA (control) and into the identical buffer after exposure of the monoclonal antibody to an electric potential (redox) according to an embodiment of the present invention.

FIG. 3 is a graph showing the aPS, aCL, aPE, and aPC binding profiles (as measured by OD) of a CD 63 monoclonal antibody in a diluent buffer containing ABP (control) and into an identical buffer after treatment of the monoclonal antibody with an electric potential (redox) according to an embodiment of the present invention. Similarly, the monoclonal was diluted into a buffer containing BSA (control) and into the identical buffer after exposure of the monoclonal antibody to an electric potential (redox) according to an embodiment of the present invention.

FIG. 4 is a graph showing the amount of aPS, aCL, aPE, and aPC binding (as measured by OD) of a beta$_2$glycoprotein-I ($\beta_2$GP-I) monoclonal antibody in an ABP containing buffer diluent (control), and in an ABP buffer diluent after exposure of the monoclonal antibody to an electric potential according to an embodiment of the present invention. Similarly, the monoclonal was diluted into a buffer containing BSA (control) and into the identical buffer after exposure of the monoclonal antibody to an electric potential (redox) according to an embodiment of the present invention.

FIG. 5 is a graph showing the aPS, aCL, aPE, and aPC binding profiles (as measured by OD) of a monoclonal antibody to clotting factor VII. This particular monoclonal was refractory to oxidative alterations and no aPL unmasking was observed.

FIG. 6 is a graph showing the aPS, aCL, aPE, and aPC binding profiles (as measured by OD) of a monoclonal antibody to clotting factor IX. Notice that in the diluent buffer containing ABP factor IX binds to the negatively charged phospholipids PS and CL (control), thus a positive monoclonal anti-factor IX reaction is seen as aPS and aCL. Redox exposure via EMF had no masking effect upon Factor IX binding in the ABP diluent. In contrast, in the ABS diluent (control) where no factor IX is present, no aPL activity is observed. However, after redox exposure, both aPE and aPC activities are unmasked.

FIG. 7 is a graph showing the aPS, aCL, aPE, and aPC binding profiles (as measured by OD) of an IgG1 monoclonal antibody sold commercially as an IgG isotype control. In this graph a comparison is made of the differential effects of two different oxidizing agents, hemin and EMF. Details are provided in the figure legend.

FIG. 8 as in FIG. 5 is a graph showing the aPS, aCL, aPE, and aPC binding profiles (as measured by OD) of a monoclonal antibody to the CD 44 antigen. This monoclonal antibody is not significantly altered in its binding activity by oxidizing agent, hemin or EMF. The monoclonal does, however, continue to bind its cell surface antigen.

FIG. 9 is a graph showing the aPS, aCL, aPE, and aPC binding profiles (as measured by OD) of a monoclonal antibody to platelet antigen, IIb-IIIa. In an ABP containing dilution buffer (control) no activity is seen as aPS or aCL. After the monoclonal in suspension was treated with an electric potential (redox) according to an embodiment of the present invention both aPS and aCL became unmasked as shown by using this buffer diluent. In the BSA containing buffer diluent (control) no activity to aPS or aCL was observed, thus the plasma proteins bound by the negatively charged PS and CL in the ABP buffer diluent was not present in the BSA containing buffer diluent. Treatment of the monoclonal with an electric potential (redox) according to an embodiment of the present invention caused an increase in strength of the aPE and aPC signals in the BSA containing buffer.

FIG. 10(a) and (b) are graphs showing the effect of EMF exposure on a monoclonal antibody produced to a plasma membrane antigen found on the murine tumor cell line SP2/0. This monoclonal antibody was tailor made for the express purpose of controlling for the proprietary variables that may exist in commercially prepared monoclonal antibody preparations. For example, might the suspension solutions used by commercial monoclonal antibody producers be contaminated with animal serum as residual from the monoclonal culture growth media? Such contamination could interfere with masking and/or unmasking observations of the mouse monoclonals.

As shown in FIG. 10, the experimental design allowed for testing of the culture media by itself, the culture media containing the monoclonal antibody, the culture media after exposure to EMF and the culture media containing the monoclonal antibody after EMF exposure. In addition, we had access to the monoclonal antibody concentrated by using a protein A affinity column (1.46 mg/ml) for further testing. FIG. 10 shows that all aPL unmasking was detected after the monoclonal antibody was treated by EMF and this was observed whether detection was in the ABP containing diluent buffer or the BSA containing buffer diluent.

FIG. 11 is a graph showing the effect of EMF oxidation over time using the monoclonal antibody anti-glycophorin A. This is the identical monoclonal antibody preparation that is shown in FIG. 1. FIG. 11 demonstrates that during the first minute of EMF exposure, the binding of this monoclonal to its red blood cell (RBC) target membrane antigen as measured by flow cytometry mean channel shifts (MCS), slopes downward. However, after the first minute wherein aliquots were obtained at 5 second intervals for flow cytometry, an uninterrupted EMF exposure for an additional minute caused a reversal of the downward trend and an upward shift to approximate the MCS value shown to occur after the initial 15-20 seconds of EMF exposure. A MCS shift from 401 to 386 which was observed at the 10 second interval and which corresponds to the time for unmasking the aPL depicted in FIG. 1 would not be considered significant by flow cytometry operators. Nonetheless, it has a profound effect upon the monoclonals' binding properties. Thus, the unmasking (alteration) of aPL reactivity has little effect upon the monoclonals RBC binding properties. The extended 1 minute EMF oxidation step, however, indicates that the downward alteration of binding to RBC during the first minute is reversible.

The two graphs comprising FIGS. 12A and 12B show that the oxidative treatment of the monoclonal antibodies shown also in FIG. 10 is a time and temperature reversible alteration of unmasking and masking. When stored at −80° C. there is no significant loss of aPL activity after EMF treatment. In contrast, storage at 37° C. for 4-days results in loss of aPL reactivity, however, the aPL reactivity can be recovered (unmasked) completely by exposing the monoclonal antibody suspension to another EMF treatment. This phenomenon could have important physiological disadvantages in vivo inasmuch as oxidized therapeutic monoclonal autoantibodies could appear (unmask) in areas where reactive oxygen species are generated, such as in sites of inflammation. Unmasking of these therapeutic monoclonal autoantibodies could lead to pathophysiological effects undesirable for the patient recipients. Indeed, this may be a reason why some therapeutic monoclonal antibodies have been discontinued from use because of their untoward and unanticipated side effects.

DETAILED DESCRIPTION OF THE INVENTION

The present invention relates to a method of altering the binding specificity of a monoclonal antibody.

The term "altering the binding specificity" of a monoclonal antibody refers to a process whereby a monoclonal antibody is changed or altered, such as by oxidation and reduction, so that it becomes capable of specific binding of an antigen or ligand that it had not previously been capable of specifically binding. For example, the spectrum of antibody activity may be broadened so that the monoclonal antibody binds to other antigens. The term "altering the binding specificity" may also apply to a process whereby a monoclonal antibody is changed or altered, such as by oxidation or reduction so that it becomes incapable of specific binding of an antigen or ligand that it had previously been capable of specifically binding, but it is to be understood that in this context, the term refers to a reversible change and not a permanent, irreversible change such as denaturing of the protein.

The term "monoclonal antibody" refers generally to an antibody that has been selected on the basis of binding specificity towards a particular antigen and then cloned or otherwise manufactured to produce a set of antibody molecules each having an identical molecular structure. Monoclonal antibodies for many antigens are commercially available.

In the method of the present invention, the binding specificity of a monoclonal antibody is altered by exposing the monoclonal antibody to an oxidant or to an electric current. For example, the binding specificity of a monoclonal antibody can by altered so that the monoclonal antibody is able to bind an antigen that it was not able to bind before the method was carried out.

If an oxidizing agent is used to carry out the method of the invention, the oxidizing agent can be any compound that is capable of altering the redox state of a biological molecule. More specifically, the oxidizing agent is a molecule that has the ability to be reduced by acting as an electron acceptor for other molecules that act as electron donors. Suitable oxidizing agents include many compounds that contain a coordinated (transition) metal that can participate in oxidation-reduction reactions, for example a redox capable metal such as iron that can alternate between its ferric and ferrous states. Other examples of oxidizing agents include, but are not limited to hemin and the coordinated magnesium metal in chlorophyll molecules, sodium periodate ($NaIO_4$) and potassium permanganate ($KMnO_4$). Typically, when a transitional metal oxidizing agent is used, a mixture of the monoclonal antibody and the oxidizing agent must be incubated for a period of time, typically for 12-24 hours. The oxidizing agent should be used at a concentration sufficient to alter the binding specificity of the monoclonal antibody, but not at a concentration that might destroy or denature the monoclonal antibody. It has been found that different types of monoclonal antibodies can interact differently with different antioxidants.

If a DC electric current is used to carry out the method of the invention, the method may be carried out by any means of delivering an electric current, such as by immersing positive and negative electrodes into a conductive solution containing the sample to be treated. A solution containing a monoclonal antibody is exposed to an electric potential of a sufficient magnitude and of a sufficient duration to alter the binding specificity of the monoclonal antibody. It has been found that positive results may be obtained by exposing a solution to an electric potential of 6-24 volts for a few seconds to a few minutes. An extended exposure to an electric current may result in reversal of the alteration of the binding specificity. This has been seen by using a glycophorin A monoclonal antibody and flow cytometry and measuring the antibody's reactivity to red blood cells overtime of EMF exposure. FIG. 11 shows a reduction in the mean channel shift (MCS) as EMF exposure increases at 5 second intervals during the first 60 seconds. However, the application of an additional minute EMF exposure (2-minutes total) causes a reversal of the downward trend and an increase in the MCS value.

Without being bound to a specific theory, it is believed that exposure of a monoclonal antibody to the oxidizing agent or electric current can oxidize and/or reduce an antigen binding site in the Fab portion of the monoclonal antibody. It has been found in oxidation experiments conducted with IVIg and using detection by monoclonal anti-nitrotyrosine antibodies that IgG that has been exposed to oxidation by hemin has a greater degree of nitrosylation than non-treated IgG. Accordingly, it can be theorized that a similar mechanism might be operative with monoclonal antibodies and that the alteration of the antigen binding site of the monoclonal antibody is effected by reversible nitrosylation of aromatic ring containing amino acids (e.g., tyrosine and tryptophan) in and around the antibody hypervariable region, which may produce conformational changes in the antigen binding site.

Whether a particular monoclonal antibody of interest is one that has a binding specificity that can be altered by changing its redox state and the effectiveness of any set of conditions for altering the binding specificity of the monoclonal antibody of interest may be readily determined by subjecting the monoclonal antibody to a change in redox state by, for example, exposing the monoclonal antibody to an oxidizing agent or electric current and then using ELISA or other ligand-receptor assays to determine whether the binding specificity of the monoclonal antibody has been altered. In other words, an assay of a monoclonal antibody can be carried out before and after the monoclonal antibody is subjected to a change in redox conditions to see whether the process has altered the binding specificity of the monoclonal antibody. For example, the best oxidizing agent or method to alter a specific monoclonal antibody can be readily determined by simple experimentation. Experimental data have shown that different oxidizing agents can unmask different autoantibody specificities.

A further aspect of the present invention is a monoclonal antibody that has been altered by exposure to an oxidizing agent or electric current. As explained more fully in the examples below, it has been found to date that the binding specificity of the following monoclonal antibodies can be altered to change their binding profile with respect to at least one of cardiolipin, phosphatidylcholine, phosphatidylethanolamine and phosphatidylserine: an anti-glycophorin A monoclonal antibody; an anti-CXCR4 monoclonal antibody; a CD 63 monoclonal antibody; a $B_2$GP-1 monoclonal antibody; an anti-platelet IIb-IIIa monoclonal antibody; and a gamma 1 mouse isotype control monoclonal antibody. Alterations in binding properties of a monoclonal antibody to Factor VII and a monoclonal antibody to CD 44 as well as a monoclonal antibody to Factor IX were dependent upon the dilution buffers used for the ELISA testing.

EXAMPLES

Having described the invention, the following examples are given to illustrate specific applications of the invention, including the best mode now known to perform the invention.

These specific examples are not intended to limit the scope of the invention described in this application.

Regarding each of the described herein, unless otherwise noted, the following procedure was typically used: 250 μl of monoclonal antibody was used directly from the vial or bottle supplied by the commercial vendor. It was placed as a bubble on a parafilm sheet. Graphite electrodes were connected to the positive and negative terminals of 6-9 volt battery or a power source (BK Precision) set at 8-volts and were submersed into the bubble solution containing monoclonal antibodies for 10 seconds. (Where noted herein, an alternative treatment was used in which the monoclonal antibody was combined with hemin and the mixture was incubated, with rocking or shaking, at 36° C. for a period of 12-24 hours.) Following the treatment with electric current or with hemin, a sample of the monoclonal antibody was tested for the presence of antiphospholipid antibodies (aPL) using a comprehensive in-house ELISA aPL format that provides separate aPL test results. The testing procedure is described in greater detail in the following publications, incorporated herein by reference: Wagenknecht, D R, et al., The Evolution, Evaluation and Interpretation of Antiphospholipid Antibody Assays, Clinical Immunology Newsletter, Vol. 15, No. 2/3 (1995) pp. 28-38 and McIntyre, J A, et al., Frequency and Specificities of Antiphospholipid Antibodies (aPL) in Volunteer Blood Donors, Immunobiology 207(1): 59-63, 2003.

Four aPL specificities were assessed, 1) aPS=antiphosphatidylserine, 2) aCL=anticardiolipin, 3) aPE=antiphosphatidylethanolamine, and 4) aPC=antiphosphatidylcholine. Each monoclonal antibody sample, before and after oxidation was diluted 1/10 into and assessed in the presence (dependent) and absence (independent) of a TRIS buffer diluents supplemented with either 10% adult bovine plasma (ABP), which contains the phospholipid-binding plasma proteins or 1% bovine serum albumin, (BSA, which is devoid of phospholipid-binding plasma proteins), respectively.

Figure 7:
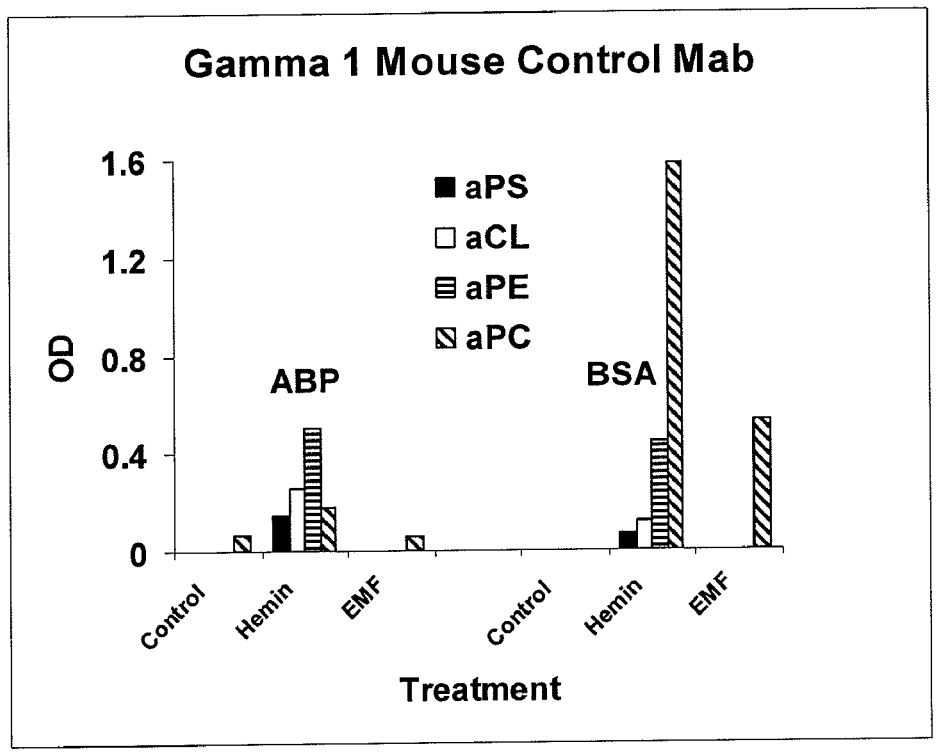

With the exception of FIGS. 7, 10 and 12, the monoclonal antibodies used for the figures shown in this application were to human proteins and prepared and sold commercially for hospital laboratory use. These murine monoclonal antibodies represented subclasses IgG1, IgG2a and IgG2b. Thus, all IgG subclass are susceptible to oxidation-reduction (redox) alterations. Similar to published polyclonal antibody data, we detect unmasking and masking of monoclonal antibody reactivity subsequent to redox reactions. All ELISA data cited were done in triplicate. We used an in-house aPL ELISA to test for binding alterations resulting from oxidation-reduction reactions because we have years of experience with this assay and our laboratory does thousands of these tests yearly. Procedural descriptions of the assay can be found in the publications listed above. All monoclonal antibody suspensions were diluted 1/10 before testing in an ELISA unless otherwise stated.

The results in the aPL specificities obtained for the various experiments described herein are given in the accompanying figures. The positive/negative findings are expressed in terms of optical density (OD). In describing the results herein, the term "unmasking" refers generally to the condition in which an alteration of binding specificity of a monoclonal antibody is observed, such as, for example, where an enhanced binding to a phospholipid antigen is observed.

Example 1

Figure 1:
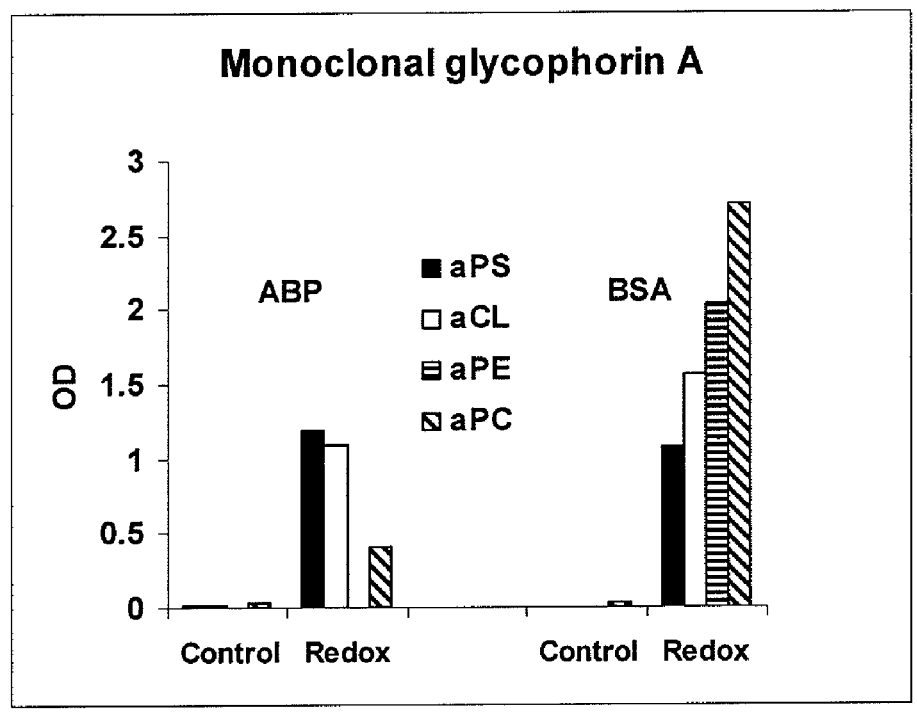

A 250 μl bubble of the manufacturer's solution containing a mouse monoclonal IgG2b antibody to human glycophorin A was placed on a parafilm platform. The solution was exposed to 10 seconds of 8-volt EMF by immersing two electrodes (anode and cathode) for 10 seconds with a power source set at 8 volts. Each monoclonal antibody solution was assayed before and after oxidation for the following binding specificities: antiphosphatidylserine (aPS), anticardiolipin (aCL), antiphosphatidylethanolamine (aPE), and antiphosphatidylcholine (aPC) The control and redox exposed solutions were then assayed for aPS, aCL, aPE and aPC binding specificities each diluted 1/10 into separate TRIS diluent buffers, one supplemented with 10% adult bovine plasma (ABP) and the other supplemented with 1% bovine serum albumin (BSA). The binding profiles for the diluents containing ABP and BSA and the anti-glycophorin A monoclonal antibody before EMF treatment ("control") and after EMF treatment ("redox") are shown in FIG. 1. It can be seen in FIG. 1 that untreated, control, glycophorin A had no antiphospholipid antibody (aPL) activity, but after redox exposure by using electromotive force (EMF), significant aPL reactivity was detected. The ELISA for aPL detection was performed in two diluents containing either 10% adult bovine plasma (ABP) or 1% bovine serum albumin (BSA), both in TRIS buffer. The ABP supplements the buffer with plasma proteins as certain aPL require phospholipid binding proteins to become detectable whereas aPL independent of phospholipid binding proteins will bind without supplemental plasma proteins. In this example, binding to PS is equivocal in both buffers. Binding to PE is only observed in the BSA buffer indicating that the aPE is not binding to PE in the presence of ABP because it is inhibited by a plasma protein that has a higher affinity for binding PE than the aPE.

Example 2

Figure 2:
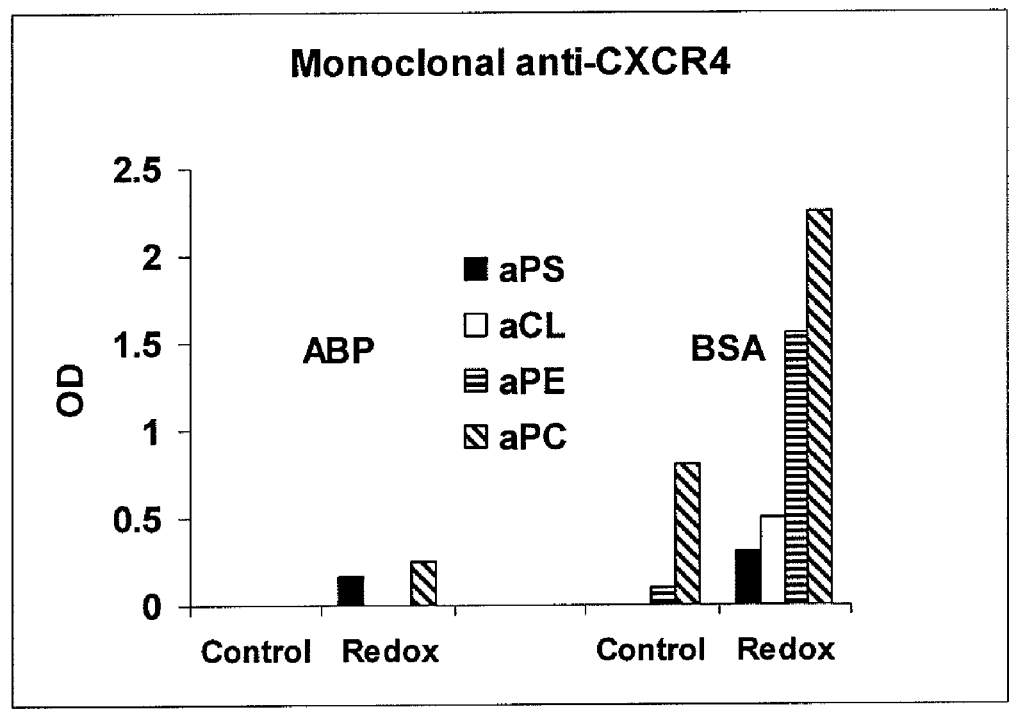

Example 1 was repeated, except that a mouse anti-CXCR4 monoclonal antibody, a co-receptor for the HIV infection of CD4 positive cells, was used as the monoclonal antibody instead of an anti-glycophorin A monoclonal antibody. The treatment and testing format was the same as for FIG. 1. The binding profiles for the diluents containing ABP and BSA and the anti-CXCR4 monoclonal antibody before EMF treatment ("control") and after EMF treatment ("redox") are shown in FIG. 2. As shown in FIG. 2, little activity is noted in the ABP containing buffer diluent. Significant aPC reactivity is seen in the control sample diluted into the buffer containing BSA which increases in the redox exposed sample. In addition, significant aPE, aCL and aPS reactivities appear subsequent to oxidation of the monoclonal and dilution into a buffer containing BSA.

Example 3

Figure 3:
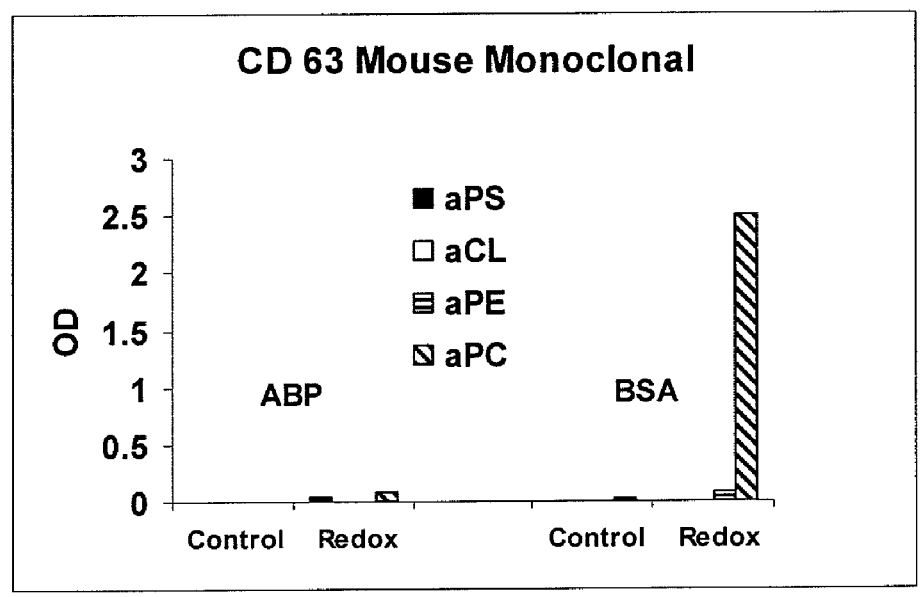

Example 1 was repeated, except that a CD 63 monoclonal antibody was used as the monoclonal antibody instead of an anti-glycophorin A monoclonal antibody. The format of the ELISA testing of an IgG1 monoclonal antibody to CD 63 was identical to that described in FIGS. 1 and 2. The binding profiles for the diluents containing ABP and BSA and the CD 63 monoclonal antibody before EMF treatment ("control") and after EMF treatment ("redox") are shown in FIG. 3. As shown in FIG. 3, oxidation of this monoclonal by EMF showed a single alteration, the appearance of aPC in the BSA buffer sample.

Example 4

Figure 4:
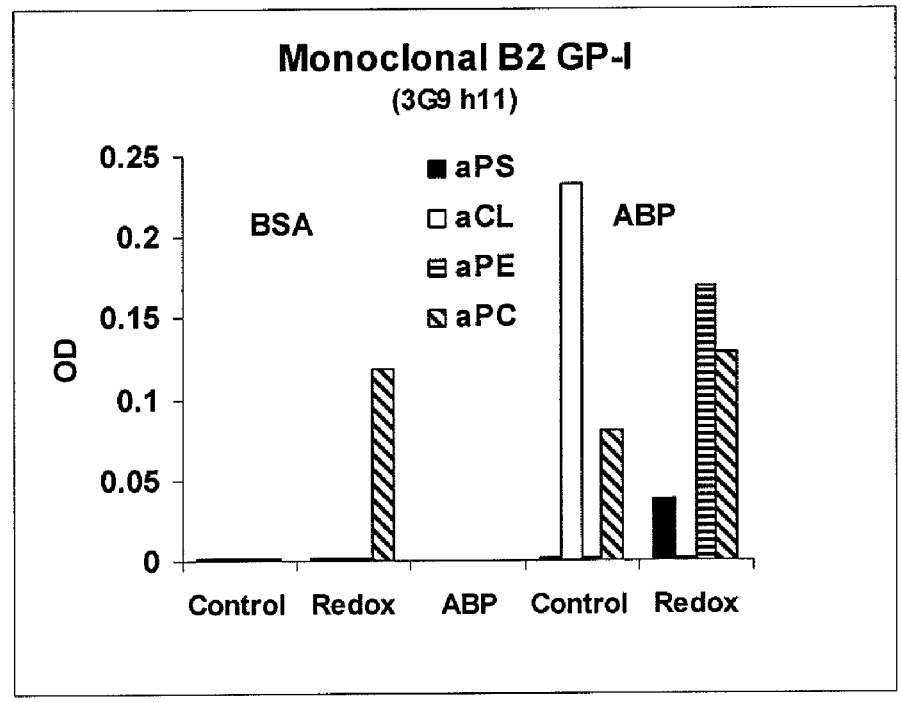

Example 1 was repeated, except that a monoclonal antibody to a plasma protein, beta2 glycoprotein I ($\beta_2$GP-I) was used as the monoclonal antibody instead of an anti-glycophorin A monoclonal antibody. The binding profiles for the diluents containing ABP and BSA and the $\beta_2$GP-I monoclonal antibody before EMF treatment ("control") and after EMF treatment ("redox") are shown in FIG. 4. Interesting aspects in FIG. 4 are in the ABP containing buffer. $\beta_2$GP-I is not present in the BSA buffer dilution, but is present in the ABP buffer diluent. $\beta_2$GP-I binds to cardiolipin and is recognized by the monoclonal as shown in the control sample. However, after redox oxidation by EMF, the monoclonal fails to recognize its $\beta_2$GP-I antigen. Thus oxidation has altered the monoclonals' binding site for $\beta_2$GP-I. However, after oxidation of this monoclonal there is reactivity as an aPE antibody in the ABP containing buffer diluent and aPC reactivity in the BSA containing diluent. Thus, there is simultaneous masking and unmasking of this monoclonals' aPL reactivities.

Example 5

Figure 5:
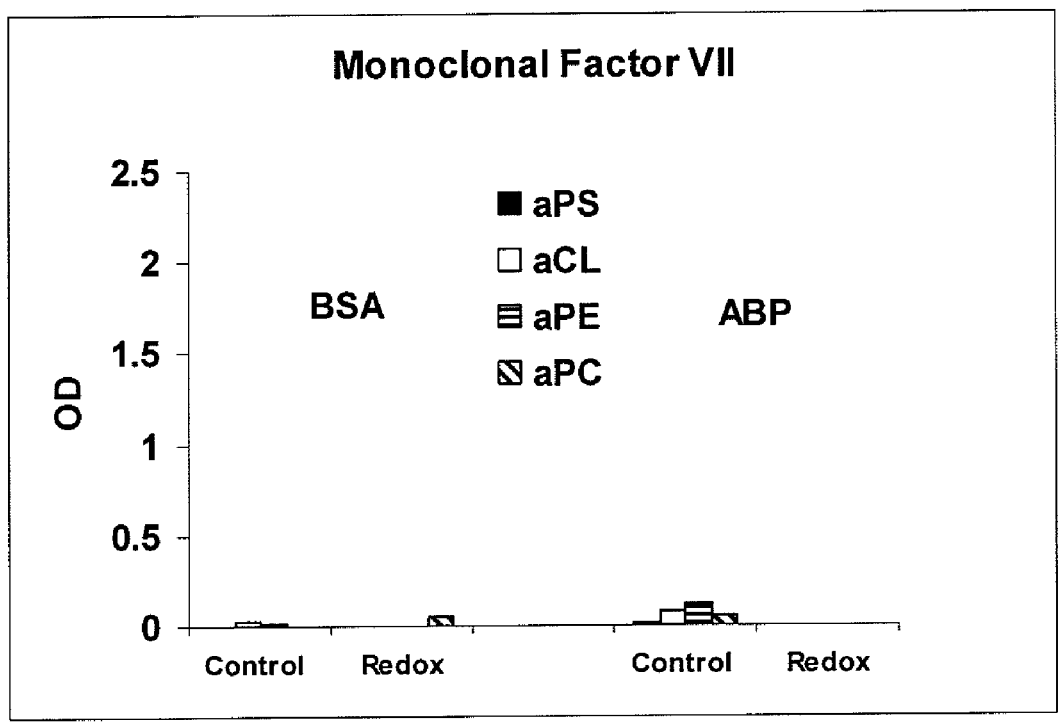

Example 1 was repeated, except that an anti-factor VII monoclonal antibody was used as the monoclonal antibody instead of an anti-glycophorin A monoclonal antibody. The binding profiles for the diluents containing ABP and BSA and the anti-factor VII monoclonal antibody before EMF treatment ("control") and after EMF treatment ("redox") are shown in FIG. 5. As shown in FIG. 5, no redox alterations were observed for aPL binding.

Example 6

Figure 6:
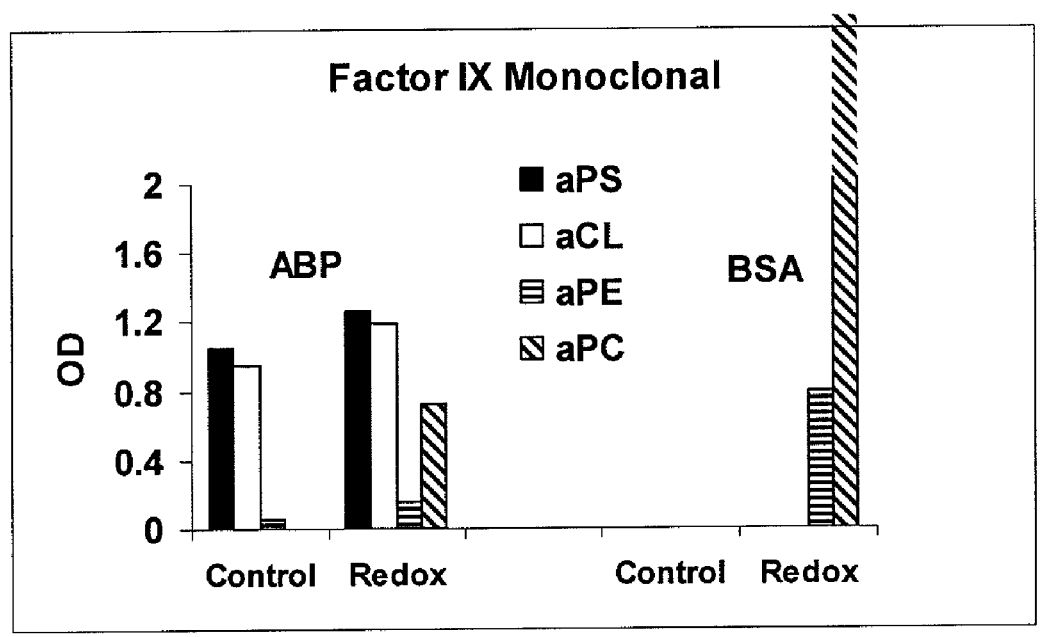

Example 1 was repeated, except that a factor IX monoclonal antibody was used as the monoclonal antibody instead of an anti-glycophorin A monoclonal antibody. The binding profiles for the diluents containing ABP and BSA and the factor XI monoclonal antibody before EMF treatment ("control") and after EMF treatment ("redox") are shown in FIG. 6. As shown in FIG. 6, the IgG monoclonal antibody to factor IX is not altered (masked) by redox exposure as shown by the fact that factor IX, present in the ABP buffer diluent, is equally recognizable by the antibody in the control and redox samples. In the BSA diluent, because no factor IX is available, the control is negative but both aPE and aPC are unmasked by EMF redox exposure.

Example 7

Example 1 was repeated, except that gamma 1 mouse control monoclonal antibody was used as the monoclonal antibody instead of an anti-glycophorin A monoclonal antibody. Additionally, an alternative oxidative treatment was carried out using hemin under the conditions described above. In particular, hemin, 2.5 µl (15.15 mg/ml) was added to 0.5 ml of the monoclonal antibody solution and incubated overnight at 36° C. on a rocking platform. The binding profiles for the diluents containing ABP and BSA and the gamma 1 mouse control monoclonal antibody before either hemin or EMF treatment ("control") and after "EMF" and "Hemin" treatment are shown in FIG. 7. FIG. 7 shows that that alteration of the monoclonal binding activities is affected by the oxidizing agent. In this example hemin unmasks aPS, aCL and aPE reactivities whereas EMF treatment does not. Both hemin and EMF can unmask aPC which is most notable when the monoclonal is diluted into a buffer containing BSA. The monoclonal antibody in this graph is sold commercially as an IgG isotype control antibody and its antigen of record is hemocyanin, a protein not found in the human repertoire. EMF exposure was the same as described in FIG. 1.

Example 8

Figure 8:
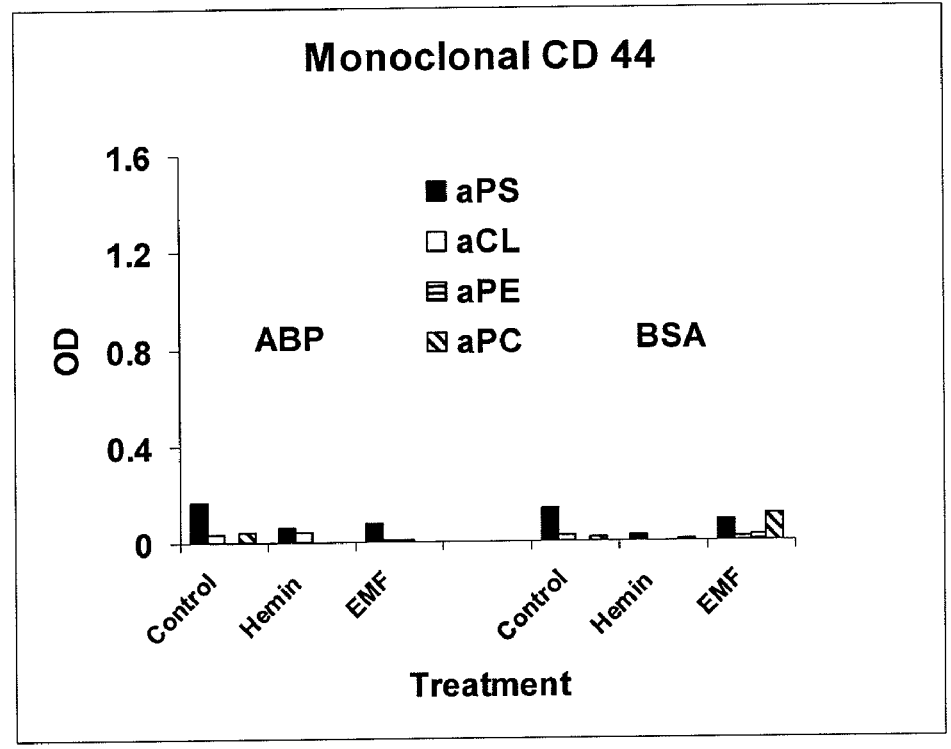

Example 1 was repeated, except that a CD 44 monoclonal antibody was used as the monoclonal antibody instead of an anti-glycophorin A monoclonal antibody. The binding profiles for the diluents containing ABP and BSA and the CD 44 monoclonal antibody before treatment ("control") and after "Hemin" or "EMF" treatment are shown in FIG. 8. FIG. 8 shows that a that a commercially produced IgG1 monoclonal antibody to the antigen CD 44 appears refractory to binding alterations when exposed to hemin and/or EMF as described in FIG. 5.

Example 9

Figure 9:
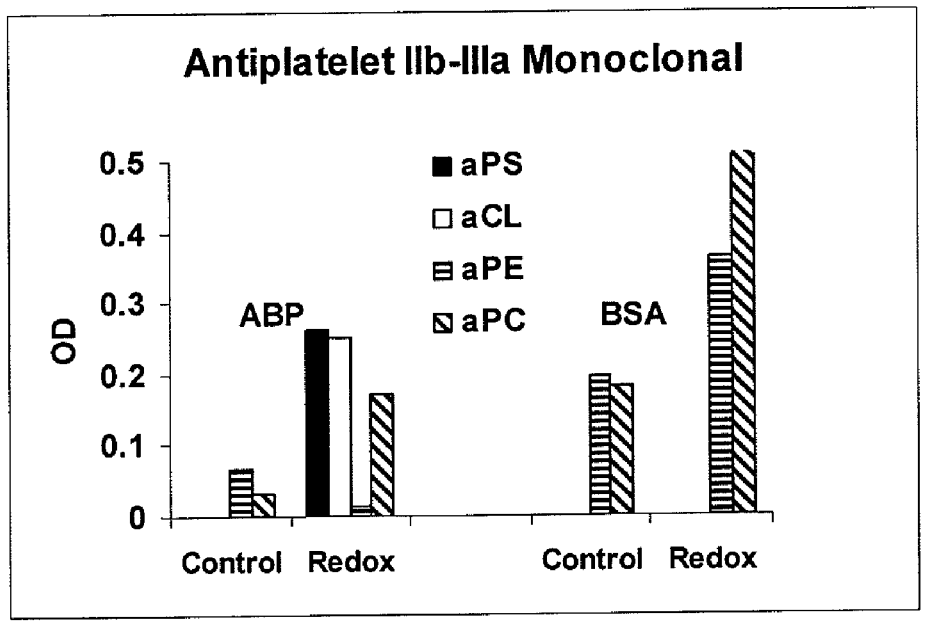

Example 1 was repeated, except that an anti-platelet IIb-IIIa mouse monoclonal antibody was used as the monoclonal antibody instead of an anti-glycophorin A monoclonal antibody. The binding profiles for the diluents containing ABP and BSA and the CD 63 mouse monoclonal antibody before EMF treatment ("control") and after EMF treatment ("redox") are shown in FIG. 9. FIG. 9 shows that shows that a commercially produced IgG1 monoclonal to the platelet antigen IIb-IIIa becomes unmasked after EMF treatment and appears as aPS and aCL in the presence of an ABP containing diluent, but not in a diluent containing BSA. The likely explanation for this observation is the presence of plasma antigens in the ABP that can bind to PS and CL and that oxidation of this monoclonal alters its binding properties.

Example 10

Figure 10A:
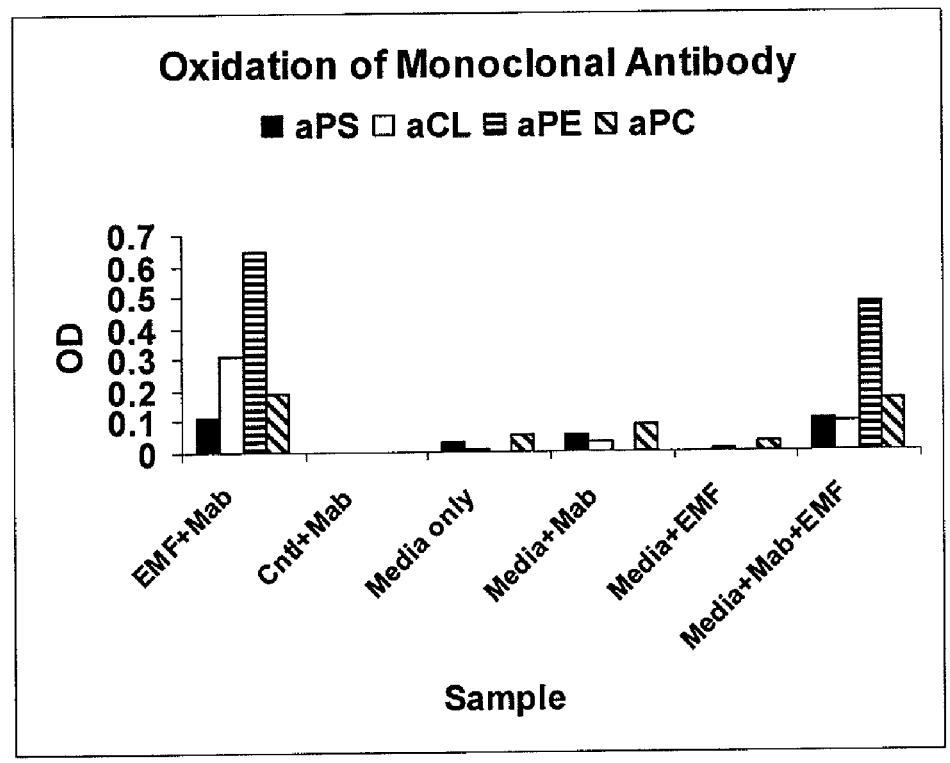
Figure 10B:
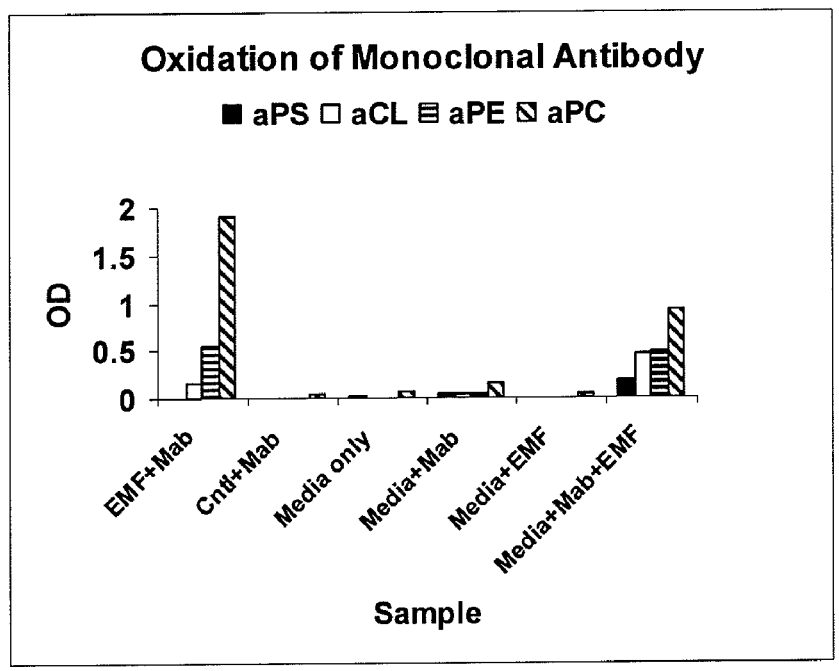

Example 1 was repeated, except that a tailor made monoclonal antibody to a murine tumor cell line SP2/0 was used as the monoclonal antibody instead of an anti-glycophorin A monoclonal antibody. This monoclonal antibody (Mab) was produced in culture media wherein all the components were known and samples of the culture media were obtained before and after growing the monoclonal to assure that all possible ELISA controls were performed. The binding profiles for the ABP (FIG. 10A) and BSA (FIG. 10B) diluents of the SP2/0 monoclonal antibody before EMF treatment ("Cntl") and after EMF treatment ("EMF") are shown. In particular, FIG. 10(A) is a graph showing the effect of EMF exposure of a monoclonal antibody (Mab) produced to a murine tumor cell line SP2/0. All culture media components were known, thus oxidation by EMF exposure as shown in the above figure unmasks aPL reactivity of this monoclonal. In this figure the EMF+Mab on the left represents oxidation of the protein-A purified monoclonal (1.46 mg/ml) diluted 1/10 into a buffer diluent containing ABP and the ELISA was developed in substrate for only 10 min. The remaining ELISA bar graphs represent substrate development for 70 min. As anticipated, the media containing the oxidized monoclonal without concentration requires significantly more development time for positive results to appear. FIG. 10(B) represents the identical samples and conditions as depicted in FIG. 10A, but the diluent buffer in this graph contained BSA. The most striking observation in the BSA diluent buffer when compared to the ABP diluent buffer is the increased signal of aPC. This may represent competition of binding between the aPC and a plasma protein in the ABP containing buffer or an antioxidant in the ABP containing buffer that is extraordinarily effective for inhibiting aPC unmasking.

Example 11

Figure 11:
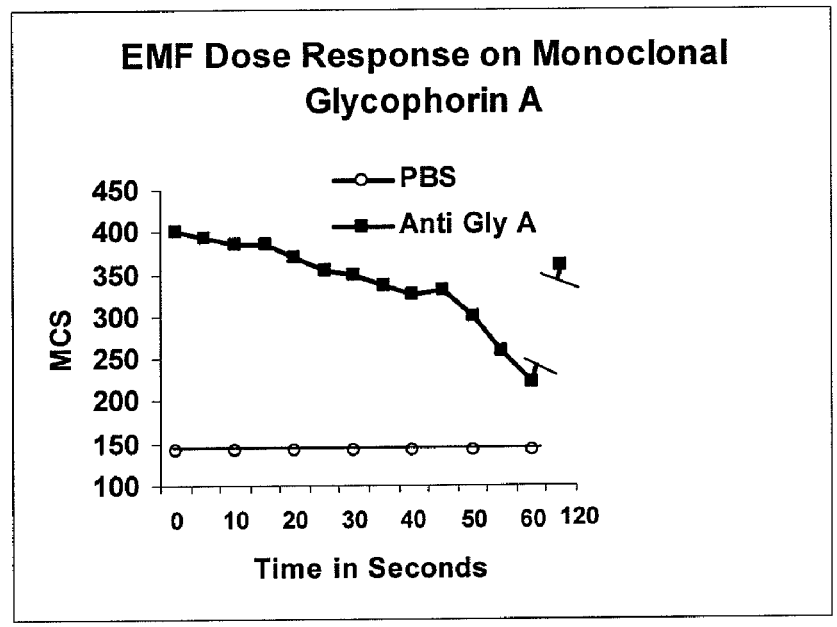

The identical anti-glycophorin A monoclonal antibody used in example 1 was used to assess the effects of EMF oxidation on the monoclonals recognition of its red blood cell (RBC) membrane target antigen. The experimental design also used a 250 µl bubble of the monoclonal antibody solution on parafilm, but a 3 µl sample was withdrawn at each 5 second interval for the first minute to test by flow cytometry for RBC binding. After 60 seconds, an additional EMF treatment was done for another 60 seconds, uninterrupted (total EMF time 2 minutes). The results of this experiment are provided in FIG. 11. In particular, FIG. 11 demonstrates by using flow cytometric analysis of red blood cell (RBC) binding, the effect of increasing the time of EMF oxidation on the identical anti-glycophorin A monoclonal antibody (anti Gly A) preparation shown in FIG. 1. During the first minute of EMF exposure an aliquot of the monoclonal antibody was sampled for RBC binding every 5 seconds. A mean channel shift (MCS) downward was observed starting at 401 before EMF application which decreased to a MCS of 223 at 60 seconds. A MCS from 401 to 386 was observed at the 10 second interval and this was shown to unmask the aPL depicted in FIG. 1. A MCS difference of 15 would not be considered significant by flow cytometry operators. After the 60 second aliquot was removed, an additional 60 seconds of EMF oxidation was applied to the remaining monoclonal antibody. The extended EMF oxidation time totaled 120 seconds and as the line graph shows, the downward trend of binding to RBC was reversed and became an MCS of 359 which was equivalent to the MCS after the initial 20 second exposure to EMF oxidation.

Example 12

The reversibility of altering the binding properties of monoclonal antibodies is shown in FIGS. 12A and 12B to be time and temperature dependent. Stored at −80° C., the oxidized monoclonal antibodies retain their aPL reactivities. Storage of the monoclonal antibodies at 37° C. shows rapid loss of the aPL binding specificities and return to their initial non-oxidized aPL status. Another exposure to EMF oxidation, however, causes the monoclonals stored at 37° C. to again unmask. In particular, as shown in FIG. 12, 4-day storage of an oxidized monoclonal antibody to murine tumor SP2/0 at 37° C. shows a loss of aPL unmasking activity that is not observed at −80° C. The aPL reactivity can be unmasked again if the 37 degree sample is exposed to another EMF treatment. Unfortunately, in this experiment, the aPE plate was dropped before its OD could be read and that's why the left panel histogram is blank for aPE. However, this experiment has been done several times with polyclonal IgG and EMF and shows loss of aPE upon 37 degree storage and recovery of aPE after a second EMF exposure.

Obviously, many modifications and variations of the present invention are possible in light of the above teachings. It is therefore to be understood that, within the scope of the appended claims, the invention may be practiced otherwise than as specifically described.

I claim:

1. A method comprising:
    providing a solution comprising a monoclonal antibody, the monoclonal antibody having a binding specificity toward a specific first antigen,
    exposing the composition to an oxidizing agent or an electric potential sufficient to effect an alteration of the binding specificity of the monoclonal antibody, and
    screening the monoclonal antibody after the composition has been exposed to the oxidizing agent or electric potential to determine whether the monoclonal antibody has a binding affinity for other antigens other than the first antigen,
    wherein the monoclonal antibody is a therapeutic agent or a candidate therapeutic agent wherein the screening is carried out to assess whether the monoclonal antibody has autoantibody activity under oxidative conditions.

2. The method of claim 1, wherein the oxidizing agent is hemin.

3. The method of claim 1, wherein exposing of the composition to an electric potential is carried out by submersing electrodes connected to a positive and negative terminal of a battery or electric power source into the solution comprising the monoclonal antibody for a predetermined period of time.

4. The method of claim 1, wherein the solution comprising the monoclonal antibody includes the commercial manufacturers' buffers, TRIS buffer, phosphate buffered saline or culture media.

5. A method of claim 1, further comprising recovering the monoclonal antibody having the altered binding specificity from the solution.

* * * * *